United States Patent
Jung et al.

(10) Patent No.: US 12,016,788 B2
(45) Date of Patent: Jun. 25, 2024

(54) NEUROMORPHIC CONTROLLED POWERED ORTHOTIC AND PROSTHETIC SYSTEM

(71) Applicants: Ranu Jung, Coral Gables, FL (US); Shah Vikram Jung, Freemont, CA (US); Brundavani Srimattirumalaparle, Glendale, AZ (US)

(72) Inventors: Ranu Jung, Coral Gables, FL (US); Shah Vikram Jung, Freemont, CA (US); Brundavani Srimattirumalaparle, Glendale, AZ (US)

(73) Assignee: Advensys, LLC, Fayetteville, AR (US)

( * ) Notice: Subject to any disclaimer, the term of this patent is extended or adjusted under 35 U.S.C. 154(b) by 0 days.

(21) Appl. No.: 14/322,326

(22) Filed: Jul. 2, 2014

(65) Prior Publication Data
US 2015/0025653 A1 Jan. 22, 2015

Related U.S. Application Data

(62) Division of application No. 12/268,430, filed on Nov. 10, 2008, now Pat. No. 8,790,282.

(51) Int. Cl.
*A61H 3/00* (2006.01)
*A61F 2/66* (2006.01)
(Continued)

(52) U.S. Cl.
CPC ............... *A61F 2/72* (2013.01); *A61F 2/66* (2013.01); *A61H 3/00* (2013.01);
(Continued)

(58) Field of Classification Search
CPC ..... A61H 3/00; A61F 2/72; A61F 2/66; A61F 2002/607
See application file for complete search history.

(56) References Cited

U.S. PATENT DOCUMENTS

| 5,367,790 A | 11/1994 | Gamow et al. |
| 5,458,143 A | 10/1995 | Herr |

(Continued)

FOREIGN PATENT DOCUMENTS

| EP | 1917920 | 5/2008 |
| WO | 017890 | 4/2004 |

OTHER PUBLICATIONS

Grillner, S., et al., *Neural Networks That Co-ordinate Locomotion and Body Orientation in Lamprey*, Trends in Neurosciences, vol. 18, Issue 6, pp. 270-279. (Year: 1995).*

(Continued)

*Primary Examiner* — Timothy A Stanis

(57) ABSTRACT

A neuromorphic controlled powered orthotic and prosthetic system and device including a custom or universal fit fixed-ankle orthosis, to stabilize or immobilize an injured lower limb or act as an ankle prosthesis, and an actuated or powered articulated false-foot connected to the fixed-ankle orthosis or the prosthesis to form an actuated articulated false-foot orthosis. Associated with or mounted on the actuated articulated false-foot, or in or on the body, are sensors for sensing the intent of the subject to move, and the movement range of the articulating false-foot or AAFO and an environmental perturbation. An actuator is used to drive the articulated false-foot orthosis. The system and device further include a controller having an electronic circuit with a biomimetic design based on knowledge of connectivity of neurons within the spinal cord of a primitive vertebrate. The system and device include an electronic circuit made from analog very large scale integrated components and discrete (Continued)

electronic components capable of autonomously generating cyclic voltage output. An integral power supply serves the portable controller and AAFO.

7 Claims, 12 Drawing Sheets

(51) Int. Cl.
*A61F 2/72* (2006.01)
*A61F 2/60* (2006.01)

(52) U.S. Cl.
CPC .. *A61F 2002/607* (2013.01); *A61H 2003/005* (2013.01); *A61H 2003/007* (2013.01); *A61H 2201/0103* (2013.01); *A61H 2201/1246* (2013.01); *A61H 2201/5007* (2013.01); *A61H 2201/5069* (2013.01); *A61H 2230/08* (2013.01)

(56) References Cited

U.S. PATENT DOCUMENTS

| | | |
|---|---|---|
| 6,171,239 B1 | 1/2001 | Humphrey |
| 6,409,692 B1 | 6/2002 | Covey |
| 7,190,141 B1 | 3/2007 | Ashrafiuon et al. |
| 7,279,009 B2 | 10/2007 | Herr et al. |
| 7,313,463 B2 | 12/2007 | Herr et al. |
| 7,416,538 B2 | 8/2008 | Katoh et al. |
| 7,418,755 B2 | 9/2008 | Bledsoe et al. |
| 7,578,799 B2 | 8/2009 | Thorsteinsson et al. |
| 7,799,091 B2 | 9/2010 | Herr et al. |
| 7,991,461 B2 | 8/2011 | Flaherty et al. |
| 8,021,317 B2 | 9/2011 | Arnold et al. |
| 8,048,007 B2 | 11/2011 | Roy |
| 8,075,633 B2 | 12/2011 | Herr et al. |
| 2003/0120385 A1 | 6/2003 | Etienne-Cummings et al. |
| 2004/0044417 A1* | 3/2004 | Gramnas ............ A61F 2/66 623/52 |
| 2004/0171971 A1 | 9/2004 | Ravikumar et al. |
| 2005/0070834 A1 | 3/2005 | Herr et al. |
| 2006/0106465 A1* | 5/2006 | Hikichi ............ A61F 2/5046 623/33 |
| 2006/0149338 A1* | 7/2006 | Flaherty ............ A61H 1/0255 607/49 |
| 2006/0155385 A1 | 7/2006 | Martin ............ A61F 2/6607 623/24 |
| 2007/0043449 A1 | 2/2007 | Herr et al. |
| 2007/0050045 A1 | 3/2007 | Clausen ............ A61F 2/66 623/24 |
| 2010/0113980 A1 | 5/2010 | Herr et al. |
| 2010/0241242 A1 | 9/2010 | Herr et al. |
| 2010/0324699 A1 | 12/2010 | Herr et al. |
| 2011/0082566 A1 | 4/2011 | Herr et al. |
| 2011/0166674 A1* | 7/2011 | Montmartin ........ A61F 2/6607 623/47 |
| 2011/0224755 A1 | 9/2011 | Arle et al. |
| 2011/0257764 A1 | 10/2011 | Herr et al. |
| 2011/0295384 A1 | 12/2011 | Herr et al. |

OTHER PUBLICATIONS

Jung, Ranu, et al., Real-Time Interaction Between a Neuromorphic Electronic Circuit and the Spinal Cord, IEEE, Sep. 2001, pp. 319-326, vol. 9 No. 3.

\* cited by examiner

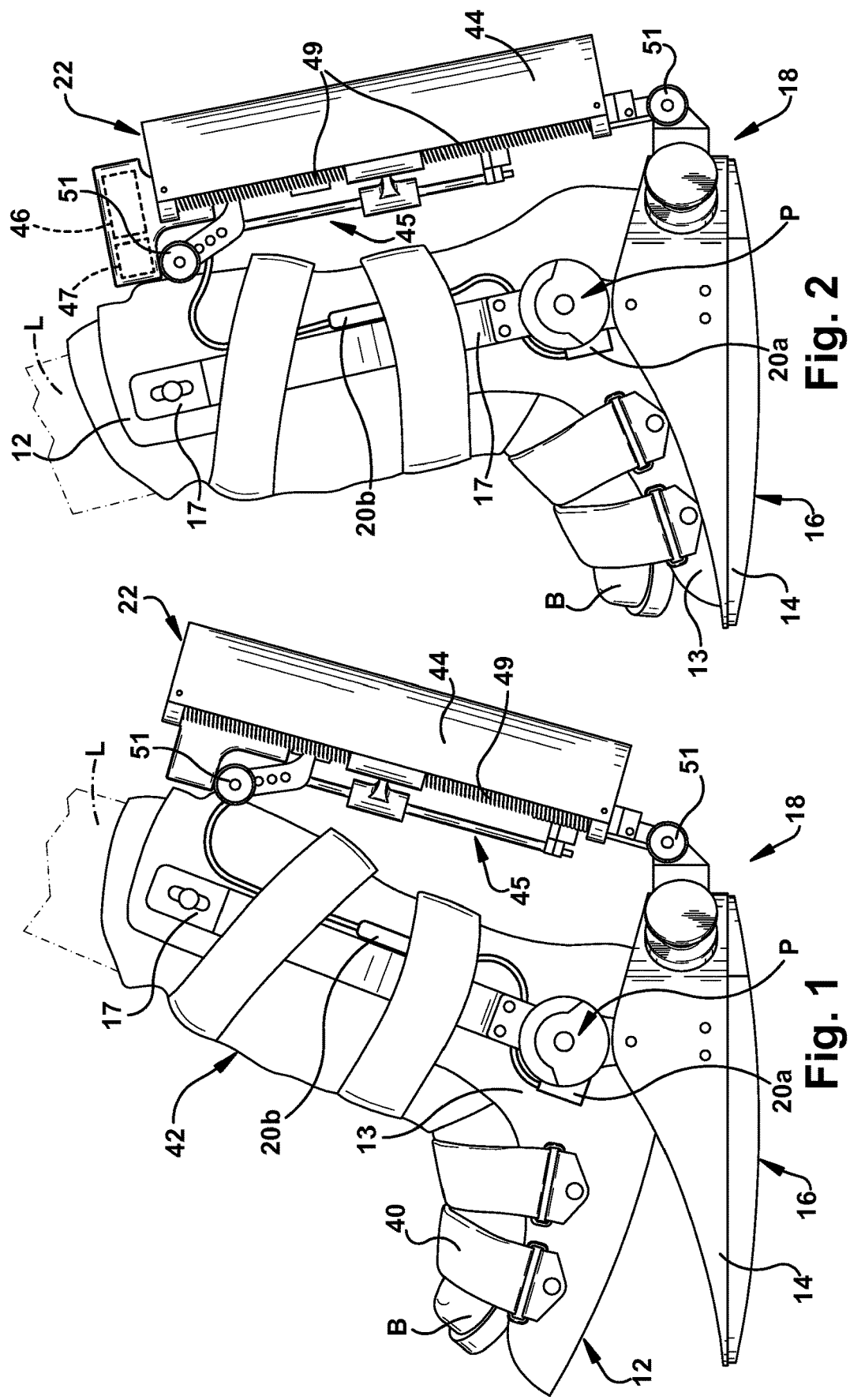

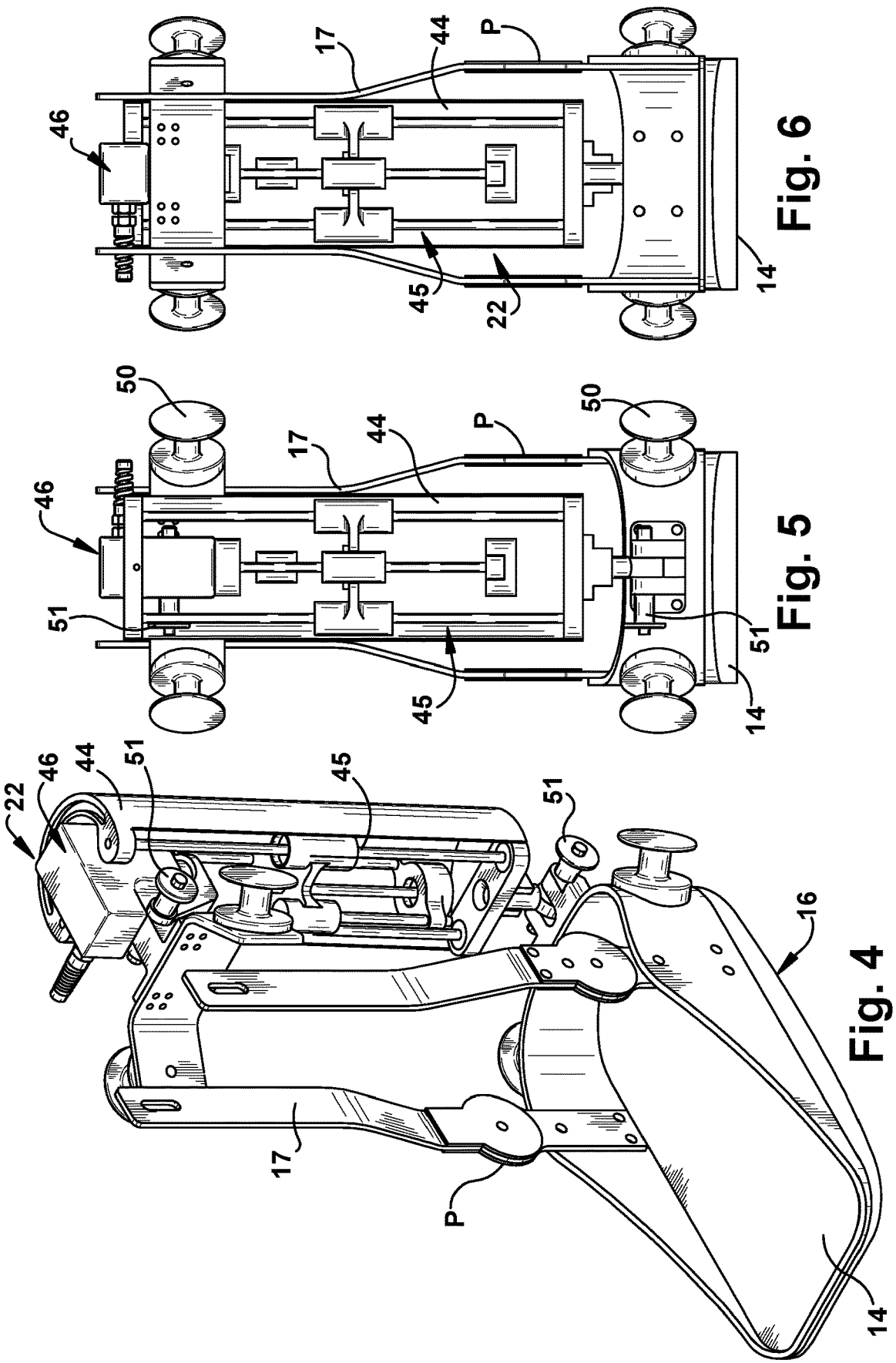

NEUROMORPHIC CONTROLLED POWERED ORTHOTIC AND PROSTHETIC SYSTEM

CROSS REFERENCE TO RELATED APPLICATIONS

The present application claims priority from U.S. provisional patent application Ser. No. 60/986,508, filed Nov. 8, 2007, the subject matter of which is incorporated herein in its entirety.

GOVERNMENT INFORMATION

The invention described in the present application was in part funded by contracts with the United States Army pursuant to Contract Nos. W911NF-04-C-0071 and W911NF-05C0122.

FIELD OF INVENTION

The present application provides a powered orthotic device with integrated computer control system for use by individuals with a transtibial (below knee) injury that prevents active control of the foot, ankle or for use by a transtibial amputee.

BACKGROUND OF THE INVENTION

In combat zones of the battlefield of today, military personnel are provided with better body protection, faster evacuation and improved medical technology and assistance. As a result, there have been dramatic reductions in battlefield mortality. However, the arms and legs of military personnel remain vulnerable to the ammunition used in today's war zones. Combat trauma to an unprotected arm or leg is often caused by high energy impact resulting in extensive soft tissue damage. Lower leg, foot and ankle injuries in the battlefield can also put soldiers at increased risk of further harm by limiting their mobility. Also, due to the severe nature of war wounds, reconstructive procedures often are delayed until months after the initial injury. After evacuation, but during the evaluation period prior to reconstructive surgery, assistive devices providing the person with mobility and independence are needed, particularly those that allow usage of the limb, as well as functional use of the upper extremities by eliminating the need for crutches and wheel chairs.

Lower leg, foot and ankle injuries have been a problem for not just the military but for the civilian population and industry as well. The National Center for Health Statistics has reported that approximately 59 million Americans have some type of foot problem and the frequency of ankle injuries in the United States varies from 1 to 10 million per year. Some of the major everyday living injuries include: automobile accidents, where 16% of occupants of passenger vehicles who were hospitalized following motor vehicle crash injuries, were diagnosed with a serious lower extremity injury and the injuries; workplace injuries, occurring at a rate of nearly 400 foot injury cases a day; and sports injuries and other activity related injuries, where the ankle is the most commonly injured joint among athletes. Such every day living injuries are further exacerbated by demographic trends such as an active aging population, diabetes and obesity.

Mobility impairment is the most frequent reason for using an assistive device. An estimated 7.4 million persons in the U.S. household population use assistive technology devices for mobility impairments. Assistive devices include crutches, canes, walkers, medical shoes and wheel chairs. Anyone ever sustaining an injury requiring crutches understands that long-term crutch use is uncomfortable, and can cause chronic shoulder pain, arthritic conditions, discomfort, muscle weakness and fatigue, and injuries to underarm arteries.

For some patients, lower extremity health problems become so severe that they must use a wheelchair. Certainly, the chronic effects of trauma or medical conditions that impair lower limb function can result in substantially decreased productivity and quality of life. In the past, lower limb orthoses provided stability, but the energy efficiency and long-term ergonomics were hindered by the rigidity of the structures. Modern orthoses provide more natural, energy efficient, and more comfortable gait by utilizing compliant materials to passively facilitate energy storage and release during locomotion. Powered orthoses, such as those disclosed in U.S. Pat. No. 7,416,538 and WO 2004/017890, also enable further advances in orthotic technology. However, improved powered orthoses enabling individuals with lower-leg injuries to walk with the same speed, energy efficiency and comfort as uninjured individuals, are desired.

SUMMARY OF THE INVENTION

The system and device of the present application provides improved locomotor function by mimicking the control of the uninjured system, and integrally linking the system and device with the neurophysiological control of the intact musculature. The present system and device substantially enhances existing technology for both military and civilian applications.

The device of the present system includes a custom or universal fit fixed-ankle orthosis, with an optional above the knee attachment, to stabilize or immobilize an injured lower limb or act as an ankle prosthesis ("AFO"), and an actuated or powered articulated false-foot connected to the fixed-ankle orthosis or prosthesis to form an actuated articulated false-foot orthosis ("AAFO"). The AAFO includes sensors associated with or mounted on the actuated articulated false-foot, or on or in the body, for sensing the intent of the subject to move, and the movement range of the articulating false-foot or AAFO and an environmental perturbation. Where the sensors are located in-body, they may be one or more implanted intrafascicular electrodes, nerve sieve electrodes, nerve cuffs, epimysial electrodes, intramuscular electrodes or electromyogram electrodes, that communicate the neurophysiological intent to move to the outside of the body through wireless technology. An actuator is used to drive the articulated false-foot orthosis.

The system and device further includes a controller having a neural network pattern generator electronic circuit. This biomimetic design of the pattern generator circuit is based on knowledge of connectivity of neurons within the spinal cord of a primitive vertebrate, which makes it a "neuromorphic" design, or a design that mimics neurobiological architectures present in the nervous system. The system and device include an electronic circuit made from analog very large scale integrated ("VLSI") components and discrete electronic components capable of autonomously generating cyclic voltage output. A power supply serves the controller and AAFO.

The AFO interconnected with the actuator and false-foot to form the AAFO, together with a controller and power supply, form a neuromorphic controlled powered orthotic and prosthetic system or "NOCS," of the present application. The present portable system and device provide "crutchless walking" to a person with an injured lower limb, which, using the sensors and controller, automatically initiates and terminates cyclic actuation of the AAFO. The system and device also automatically adjusts the speed of the cyclic control of the AAFO to match the users self selected walking velocity. Further, it responds to external perturbation and resets the cyclic control of the AAFO in response to external perturbation. The system and device minimizes the load during walking on the foot that is being supported. The system can further be utilized to provide rhythmic control of an artificial knee or ankle (or prostheses), bilateral artificial knee or ankle (or prostheses), bilateral AAFOs or to control a knee orthosis or if one hip is injured, control based signals from the other good leg may be used to control an external hip, knee or ankle orthosis or prosthesis.

BRIEF DESCRIPTION OF THE DRAWINGS

FIG. 1 is a schematic perspective view of the actuated articulated false-foot orthosis of the neuromorphic controlled powered orthotic device of the present application;

FIG. 2 is a schematic perspective view of the actuated articulated false-foot orthosis of the neuromorphic controlled powered orthotic device of the present application;

FIG. 4 is a schematic perspective view of the false-foot and actuator of the actuated articulated false-foot orthosis of the neuromorphic controlled powered orthotic device of the present application;

FIG. 5 is a rear view of the device of FIG. 4;
FIG. 6 is a front view of the device of FIG. 4.

DETAILED DESCRIPTION OF THE INVENTION

The present invention provides an integrated control system, based on principles of architecture and functions of the spinal cord of primitive vertebrates for control of rhythmic movement, to sense and control an actuated powered orthotic splint or prosthetic system for the lower limb. The system is generally referenced here as a neuromorphic controlled powered orthotic and prosthetic system or "NOCS."

Figure 3:
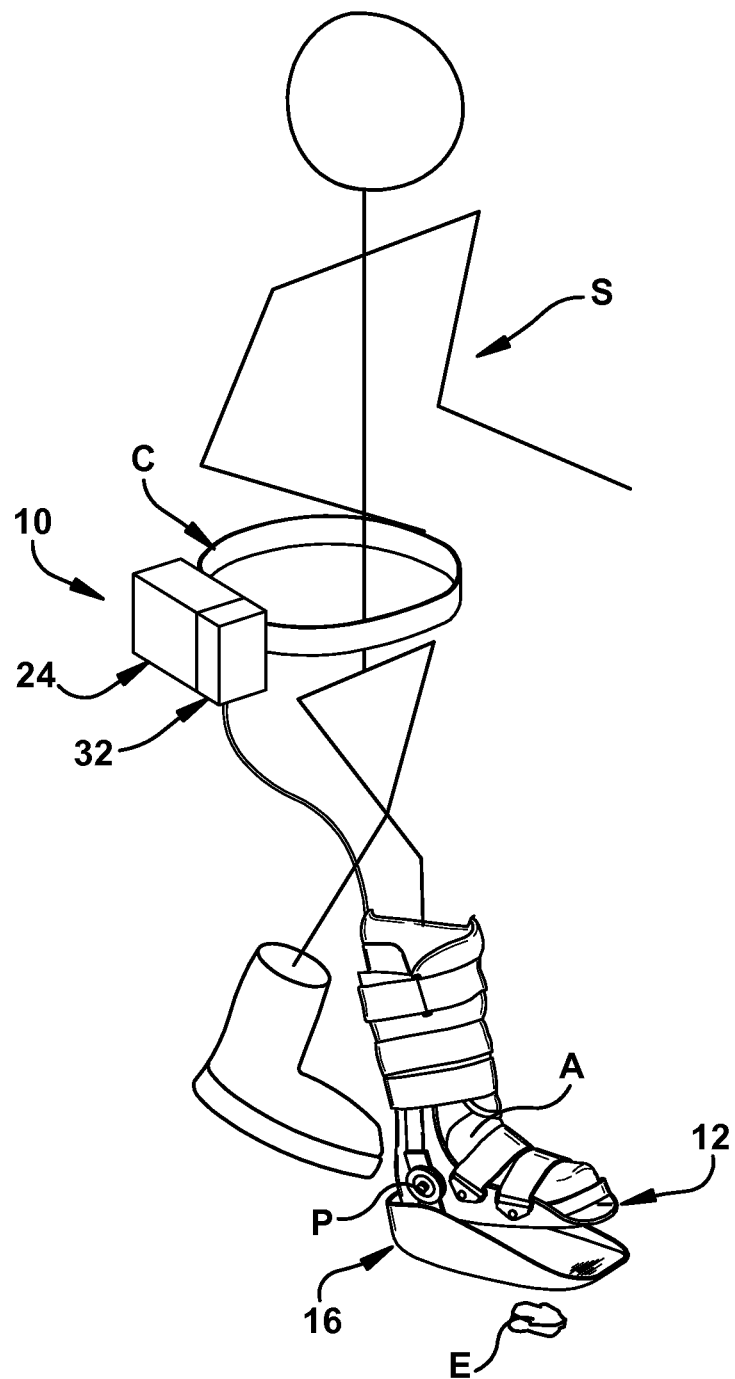
FIG. 3 is a schematic perspective view of the neuromorphic controlled powered orthotic device of the present application shown worn on a user.
Figure 7:
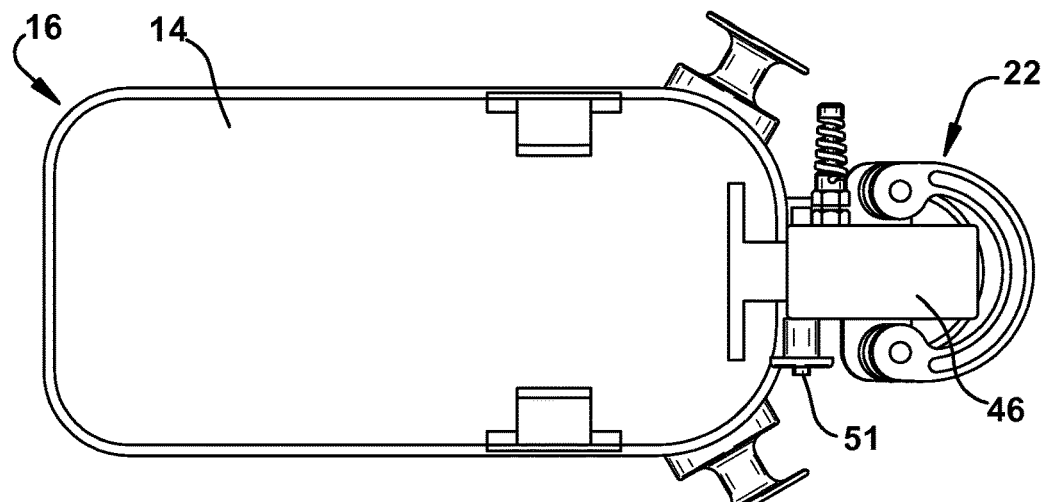
FIG. 7 is a bottom view of the device of FIG. 4.
Figure 8:
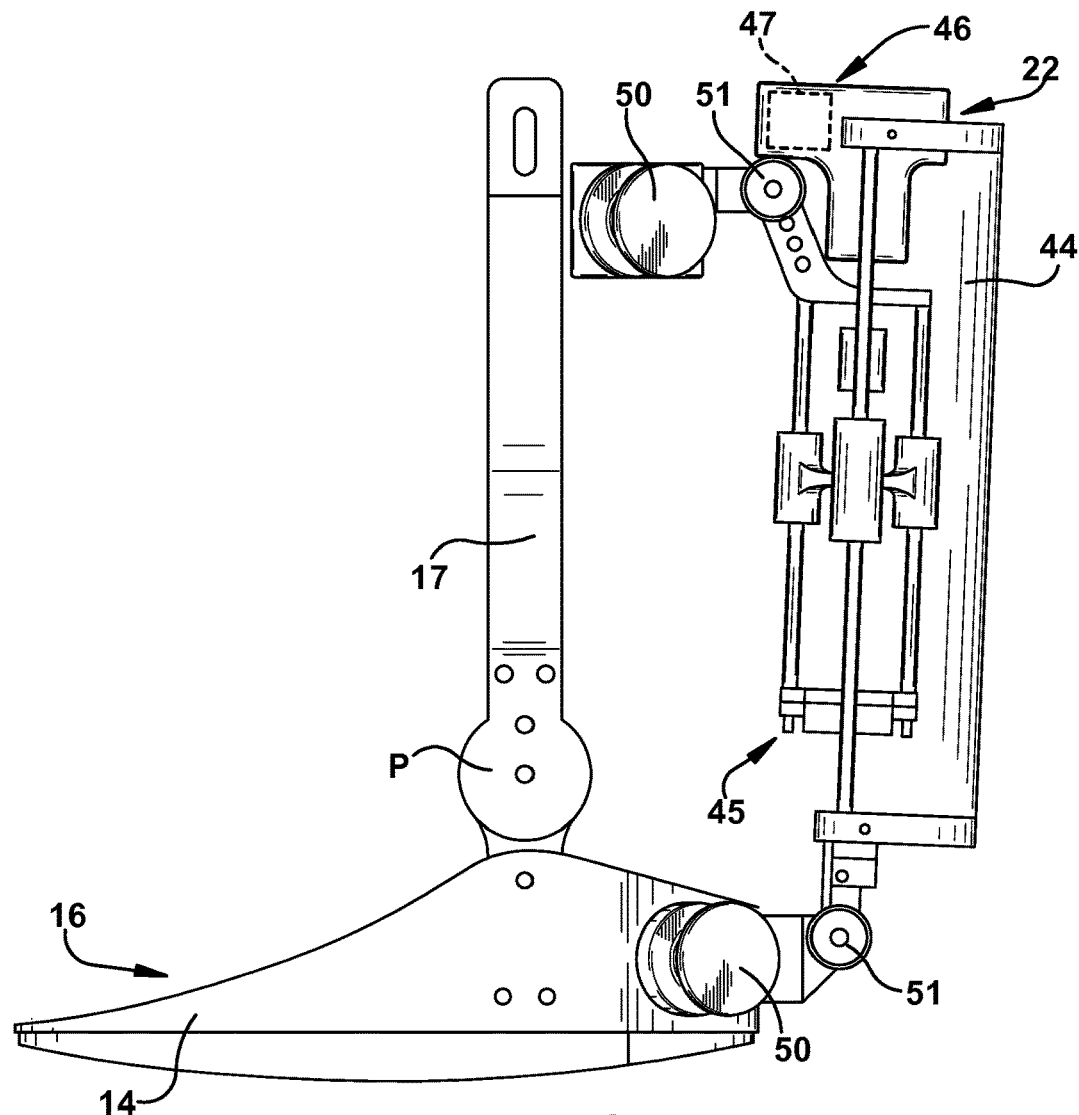
FIG. 8 is a side view of the device of FIG. 4.

The NOCS portable system and device of the present application 10, as schematically illustrated in FIG. 3, includes a custom or universal fit fixed-ankle orthosis 12 ("AFO"), with an optional above the knee attachment 14, to stabilize or immobilize an injured lower limb L or act as an ankle prosthesis, and an actuated or powered articulated false-foot 16 connected to the fixed-ankle orthosis or prosthesis 12 to form an actuated articulated false-foot orthosis 18 ("AAFO"). Associated with or mounted on the actuated articulated false-foot 16 or AAFO 18, or in or on the body, are sensors 20a. 20b. 20e for sensing the intent of the subject S to move, and the movement range of the articulating false-foot 16 or AAFO 18 with respect to an environmental perturbation E. An actuator 22 interconnects the fixed-ankle orthosis 12 and the articulated false-foot orthosis 18, and is used to drive the articulated false-foot orthosis. A controller 24 having the neural network unit pattern generator 26 or PG provided by electronic circuitry to initiate and terminate movement of the AAFO as indicated by the sensors 20a, 20b and/or 20c. The electronic circuitry uses analog components 28 and discrete electronic components 30 capable of autonomously generating cyclic voltage output. A conventional power supply 32, such as a 24 V standard battery, serves the controller 24 and the actuator 22 of the AAFO 18.

In the present application, a fixed-ankle orthosis or AFO 12 is provided which may also be a passive ankle prosthesis. The fixed-ankle orthosis 12 allows lower limb L and ankle A immobilization and forms a housing for the injured lower leg of the user or subject S. Such an AFO 12 can be fit to the user S, and universally shaped to accommodate a shoe B on a foot. Alternatively, the AFO 12 can be a universal, non-custom fit bilateral application, so that the device can be readily deployed under combat conditions, and a combat boot B of any size, right or left boot, can remain on the user S within the AFO until evacuation from the battlefield. The AFO can also be custom fit to the lower limb L, ankle and foot F.

As shown in FIGS. 1-3, the AFT 12 is preferably of a material having sufficient strength to bear loads of up to approximately 90 Kg. Examples of such construction materials include cast polypropylene or other material with similar properties, between approximately 0.2 to 0.5 inches thick. In the illustrated embodiment of FIGS. 1-2, the AFO has a universal anatomical shape of an open foot and calf support 13, for cradling the injured limb L. The AFO 12 may be reinforced in particular locations, at the back of the calf and heel, for example, to allow connection with the articulated false-foot 16 to form the actuated, powered orthosis or AAFO 18. VELCRO® or other attachment straps 40 are provided to secure the user's boot B or foot without the boot or prostheses within the support 13, and to the false-foot, and a calf liner 42 with a conventional air bladder to reduce the forces on the foot, ankle and calf.

In an alternate embodiment of the device 10 for an above the knee application, the AFO 12 is provided with a thigh support, not shown, which is interconnected with the calf support 13 at a rigid articulated knee connection, all secured to the user via Velcro straps 40 or other flexible attachments.

As shown in FIGS. 1-3, the universal fixed-ankle orthosis, AFO 12, is secured to the articulating false-foot 16. The articulating false-foot may be custom made or of off the shelf components. The shape of the AFO 12, enables it to be integrated with a variety of ankle prostheses which may serve as the false-foot 16, for example, commercially available ankle orthoses, or cam boots, such as OMNI Life-Science, the BREG Pin cam walker, DONJOY MAXTRAX ROM AIR WALKER, DONJOY ULTRA-4 ROM WALKER, and BLEDSOE Hi-Top Boot. Such commercial cam boots generally provide 40 degrees of plantar-flexion, 30 degrees of dorsi-flexion, and a range of motion adjustable in 7.5 degree increments.

As shown in FIGS. 1-8, the AAFO 18 is capable of load bearing of up to a 90 Kg person, and supports and is interconnected with the support 13 of the fixed-ankle orthosis 12. The AAFO false-foot 16 includes a base 14 having upwardly extending opposing side brackets 17, each interconnected with the base at a rotating pivot joint P. The side brackets 17 are secured to the support 13 via conventional fasteners as shown, and the brackets 17 are also surrounded by the straps 40 or other attachments securing the foot F and/or boot B within the support 13.

The base 14 of the false-foot 16 and support 13 of the AFO 12 are each secured to the actuator 22, which operates to move the support 13 with respect to the base of the false-foot 16 at the pivot point. The AAFO 18 is preferably lightweight and allows one degree of freedom of movement. The AAFO preferably operates to provide plantar-flexion between approximately 0 and 30 degrees, and less than 35 degrees at a maximum, and the user S may actively control this angle. The dorsi-flexion of the AAFO during operation is preferably between approximately 0 and 18 degrees during operation, and less than 30 degrees at a maximum, also with active control allowed. The range of motion provided by the AAFO 18 is shown by the difference in position between the support 13 and base of the false-foot 16 in FIG. 1 and FIG. 2. Eversion and inversion of the foot F is preferably less than 5 degrees, and is a passive movement of the device 18.

Where the above the knee universal fit orthosis is used to provide further offloading of the injured leg L, such an orthosis can also be utilized in a trans-tibial amputee with the articulated false-foot 16 acting as ankle prosthesis. To prevent debris from entering the space between the AFO 12 and the false-foot 16, a scree gaiter, a skirt, or dense foam can be used as a debris guard (not shown). A similar debris guard 44 is used to provide a protective cover for the actuator 22.

Several alternate methods may be used to form and connect the AFO to the articulating false-foot 18 to form the AAFO 18. FIGS. 9 to 19 illustrate possible forms and connections. The actuator 14 consists of a motor 46, a motor controller 47, and, optionally, energy storage elements 49. In the preferred embodiment, the actuator 14 provides a peak power of at least 225 Watts and a peak force of at least 1000N. The actuator weighs approximately 5-7 lbs, such that the overall weight of the AFO and AAFO is approximately 15 lbs.

Figure 9:
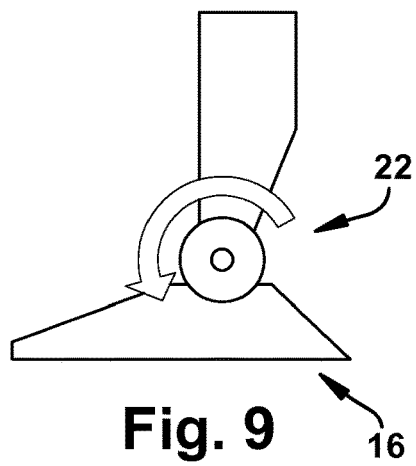
FIGS. 9, 10, 12 and 13 are schematic representations of alternative actuators for use in the neuromorphic controlled powered orthotic device of the present application.
Figure 10:
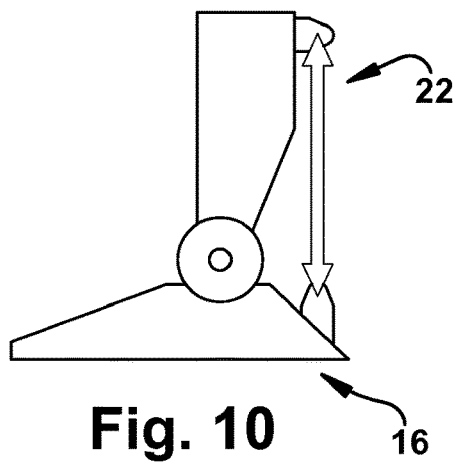
Figure 11A:
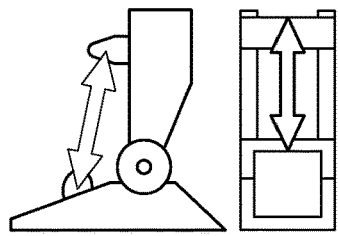
FIGS. 11a, 11b and 11c are side and front/rear views of schematic representations of alternative actuator positions mounted in the neuromorphic controlled powered orthotic device of the present application.
Figure 11B:
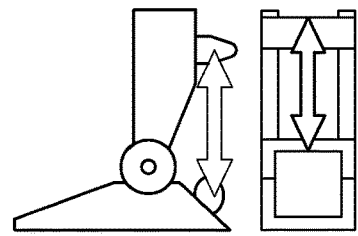
Figure 11C:
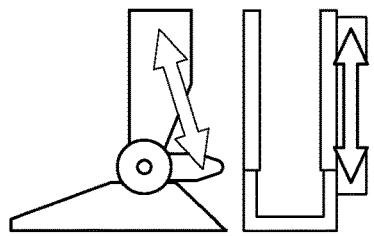

One form of actuator secured to the acute AAFO 18 includes a direct rotary drive, as shown in FIG. 9, or a linear drive is shown in FIG. 10, and of the type shown in the preferred embodiment of the present application. Within the category of linear drive actuators, there are a variety of places that the actuator could be attached to produce the desired ankle motion, as shown in FIGS. 11a-11c. Additional examples of types of actuators include a hydraulic linear actuator, consisting of conventional off the shelf components, such as a cylinder and piston driven by a working fluid. The flow of fluid is controlled by a high performance electrically controlled valve.

Alternatively, a pneumatic actuator could be used, such as a commercially available pneumatic actuator. For example, the McKibben artificial muscle pneumatic actuator may be used, which has a cylindrical flexible bladder which is covered by a braided mesh of non-stretching fibers. Both ends of the bladder are connected to the mesh. By changing the force applied to the free end of the mesh and the pressure inside the bladder, the actuator's diameter increases while the length decreases.

Figure 13:
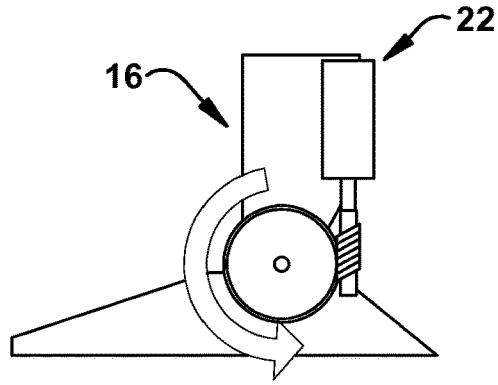
Figure 14:
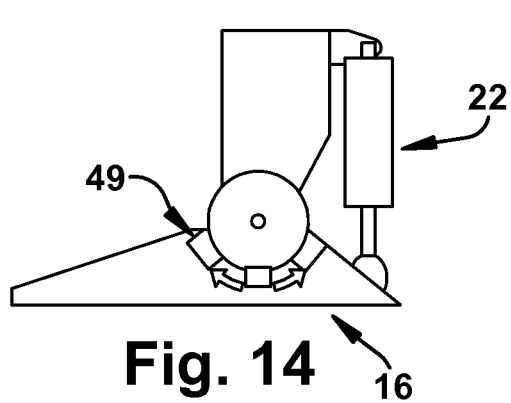
FIGS. 14-18 are side views of schematic representations of alternative energy saving mechanisms for use in the neuromorphic controlled powered orthotic device of the present application.
Figure 15:
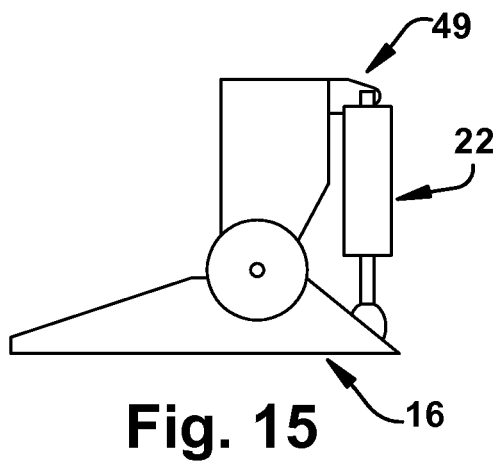

A worm gear may also be used for the actuator, as in FIG. 13. A worm gear provides a small package that generates sufficient mechanical advantage to provide the required ankle moment. In this design, a rotary motor gains mechanical advantage through a planetary gear as well as the worm gear itself.

Figure 12:
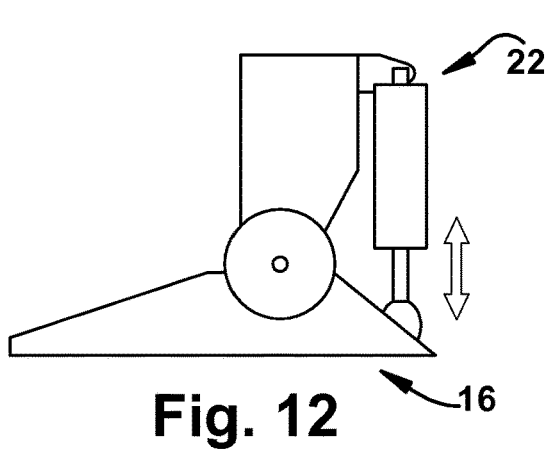

A still further actuator, shown in FIG. 12, could make use of a conventional roller screw mechanism, which converts rotary torque into a linear motion like an acme screw or ball screws. In this embodiment, an electric motor drives a set of helical rollers around a threaded shaft to product linear motion. Such a mechanism is capable of producing higher loads at the higher speeds required for this application.

Figure 16:
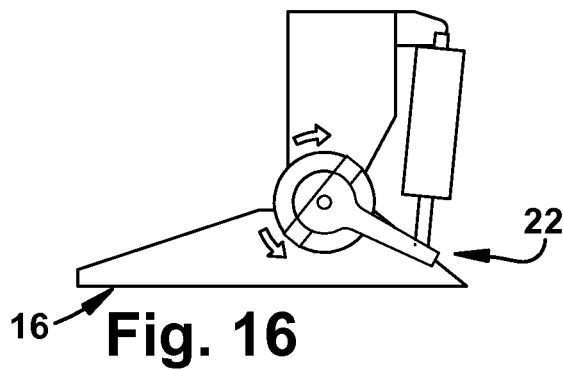
Figure 17:
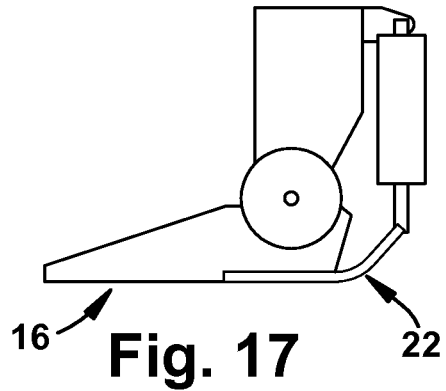

As a further option, energy storage may be utilized in conjunction with the actuator as it is connected to the false-foot 16 to reduce energy required by the mechanical actuators in the system. Examples of methods for storing and transferring kinetic energy back into the false-foot to reduce demands for peak force and peak power, include elastomeric top or bottom mounted bumpers, shown in FIGS. 14-15; a servo-saver concept, FIG. 16, is also provided in which rotational energy is reacted through a coiled spring element; a tapered leaf spring may be used, as in FIG. 17, in which a leaf spring is deformed during the heel strike of the false-foot; and pre-tensioned elastomeric bands of the type shown in FIG. 19.

Figure 18:
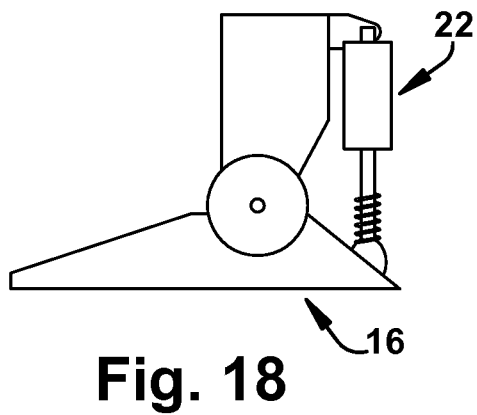
Figure 19:
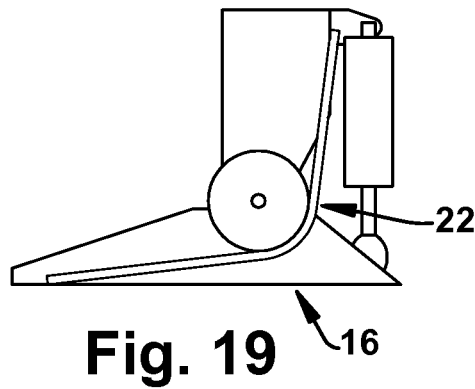

As shown in the preferred embodiment of FIGS. 1-2, and in FIG. 18, a coil spring is configured to wrap around elements of the actuator. This type of spring is commercially available in a variety of sizes and tensions, and typically of a steel alloy material. The springs are compressed as the actuator moves up/down and thus store energy during compression. There are two parallel springs that store energy as the actuator moves up, and two that are compressed as the actuator moves down. By appropriate adjustments of the timing pattern, energy is stored during part of the gait cycle and released in another part. The springs work in series with the direction of the actuator movement. Adding bungee cords mounted in parallel can further enhance the ability to store and release energy.

In the preferred embodiment shown in FIGS. 1-3, a non-custom fixed universal ankle foot orthosis or AFO 16, is interconnected with an actuated articulated false-foot orthosis or AAFO using a linear actuator 22 having a roller screw mechanism 45. The AFO is capable of use in a combat zone for stabilizing the leg of an injured soldier without removing the boot B. In FIGS. 1 and 3, the AFO 16 is shown in a toe up/dorsi-flexed position, and in FIG. 2 shows the AFO in toe down/plantar-flexed position, indicating a range of motion provided by the AAFO 18.

As shown in more detail in FIGS. 4-8, the actuator 22 includes a conventional rotary DC Maxon motor 46, having an EPOS 70/10 motor controller which converts force to linear action through the lead screw mechanism 45 shown. The motor 46 is shown within a housing mounted on the top of the actuator 22. Off the shelf McMaster-Carr tie rods support a sliding carriage moved on ball bearings using the ball screw mechanism shown. Linear springs 49 shown in FIGS. 1-2, mounted on the tie rods, and in series with the lead screw mechanism, provide the energy storage previously mentioned during dorsi-flexion and plantar-flexion. Detachable flexible cord or bungee cord may be provided as parallel energy storage elements. The bungee cord or flexible material (shown schematically in FIG. 5) can be secured at the top of the AFO and the bottom of the AAFO on posts or hook 50 shown in FIGS. 4-8. Quick disconnect mechanisms 51 are provided between the actuator 22 at the upper attachment location on the AFO, and the lower attachment location between the actuator and the false-foot 16, so that the actuator may be quickly removed or attached from the AAFO 18 on the user S.

Several types of sensors may be used to transmit position information for components of the NOCS 10. The sensors 20a, 20b, 20c are interconnected with the system controller 24 or motor controller 47 and provide accurate information about the angular excursion of the false-foot 16, sense initiation, respond to continuous movement of the user, and termination of a gait event cycle, provide feedback to the controller about the self selected walking speeds of the user S, provide information about external disturbances and perturbations and help reset the locomotor rhythm.

A first type of sensor is provided in or adjacent the pivot point P of the AAFO or in the motor 46 of the actuator. As shown in FIG. 2, the sensor 20a is illustrated mounted adjacent the pivot point P of the false-foot 16. The sensor 20a, which may be a potentiometer at the pivot point P, indicates the change in angle of the false-foot 16, or the degree of plantar-flexion or dorsi-flexion of the AAFO 18, and uses local proportional integrative derivative feedback control of the actuator motor 46 that results in linear movement of the lead screw shaft of the actuator 22. Such linear movement results in rotational movement of the false-foot 16 about the pivot point P, and a calibration process indicates linear movement in millimeters, or turns of the lead screw, relative to the angular movement in degrees.

A second type of sensor 20b is provided to sense initiation and termination of a gait event cycle, as well as continuous movement of the uninjured limb or the contralateral leg, thereby providing real-time output at the self-selected walking speed of the user S. This second sensor type may be mounted anywhere along the AAFO or AFO bracket front, back or side, an in-body sensor, on the uninjured swinging limb, on the intact portion of the injured limb or on any body part that moves at the self-selected walking pace. The output of the second sensor 20b can be a continuous signal or a periodic discrete pulse-like signal, where the pulse is generated when the sensor output goes above a predefined threshold. The output of the second sensor 20b provides feedforward input to the PG 26 of the NOCS via the auxiliary neuron as described below. The PG provides trajectory timing for driving the actuator motor 46. Although the illustrated sensor 20b, shown mounted laterally on the AAFO 18, is a gyroscope type sensor, and specifically a MEMS based gyroscope from Analog Devices, product ADXRS300, multiple sensors may be used, and multiple types of sensors may be used. Alternatively, this sensor 20b, which senses the initiation and termination of the user S may be the sole sensor used.

A third type of sensor 20c may provide information about the episodic external disturbances and perturbations and helps reset the locomotor rhythm by providing a brief input signal to the PG. The sensor 20c may be mounted on a sensor board of the controller.

Key characteristics of sensors 20a, 20b, 20c used in the NOCS are their low-profile, light weight, simple power requirements, fast response times, and low susceptibility to noise. The rotational velocity signal provided by sensor 20a may also be used to provide information to the controller neuromorphic orthotic control system, for detection of key gait events or to provide a continuous estimate of rotational velocity or orientation if the signal is integrated.

Sensors may alternatively be located on or in the user's body, or mounted on either leg. Alternatively or additionally, hip-angle sensors (commercial goniometers), tilt-sensors mounted on the shank of un-injured leg, surface electromyogram sensors may be mounted on a thigh of the injured leg or thigh or shank of un-injured leg, accelerometers; force sensitive resistors; or potentiometers operational in the range 0-35 degrees, with 180 degrees maximum, may also be used. Set forth below is a chart of the types and advantages of sensors that may be used electrodes. The output of the sensing electrodes will be processed through the electronic circuitry to provide the appropriate voltage or current analog or digital input to the PG.

| TYPE OF SENSOR | ADVANTAGES |
| --- | --- |
| Surface | Metal plate with electrolyte gel, noninvasive |
| In/On Muscle | Lower thresholds and better selectivity compared to surface electrodes |
| Intramuscular | Implanted in the muscle, multistranded Teflon coated stainless steel wire, monopolar and bipolar configurations, good tensile strength, and flexibility |
| Epimysial | Implanted under the skin: on the muscle, monopolar and bipolar configurations, less prone to mechanical failure |
| BIONs | Injected into or near the muscle, hermetically sealed glass/ceramic capsule integrated with electronics |
| Near/On Nerve | Lower threshold levels and better selectivity than the above mentioned electrodes |
| Nerve Cuffs | Monopolar, bipolar and tripolar configurations, good power efficiency, improved selectivity, comparatively stable |
| FINE | Reshape or maintain nerve geometry |
| Intrafascicular | Penetrate the epineurium and into the fascicle, selective stimulation, lower current and charge levels |
| LIFE | Stable, suitable for stimulating and recording |
| SPINE | Reduced nerve damage |
| Intraspinal Microwires | Near to normal recruitment, reduced fatigue, highly selective stimulation |

Figure 20:
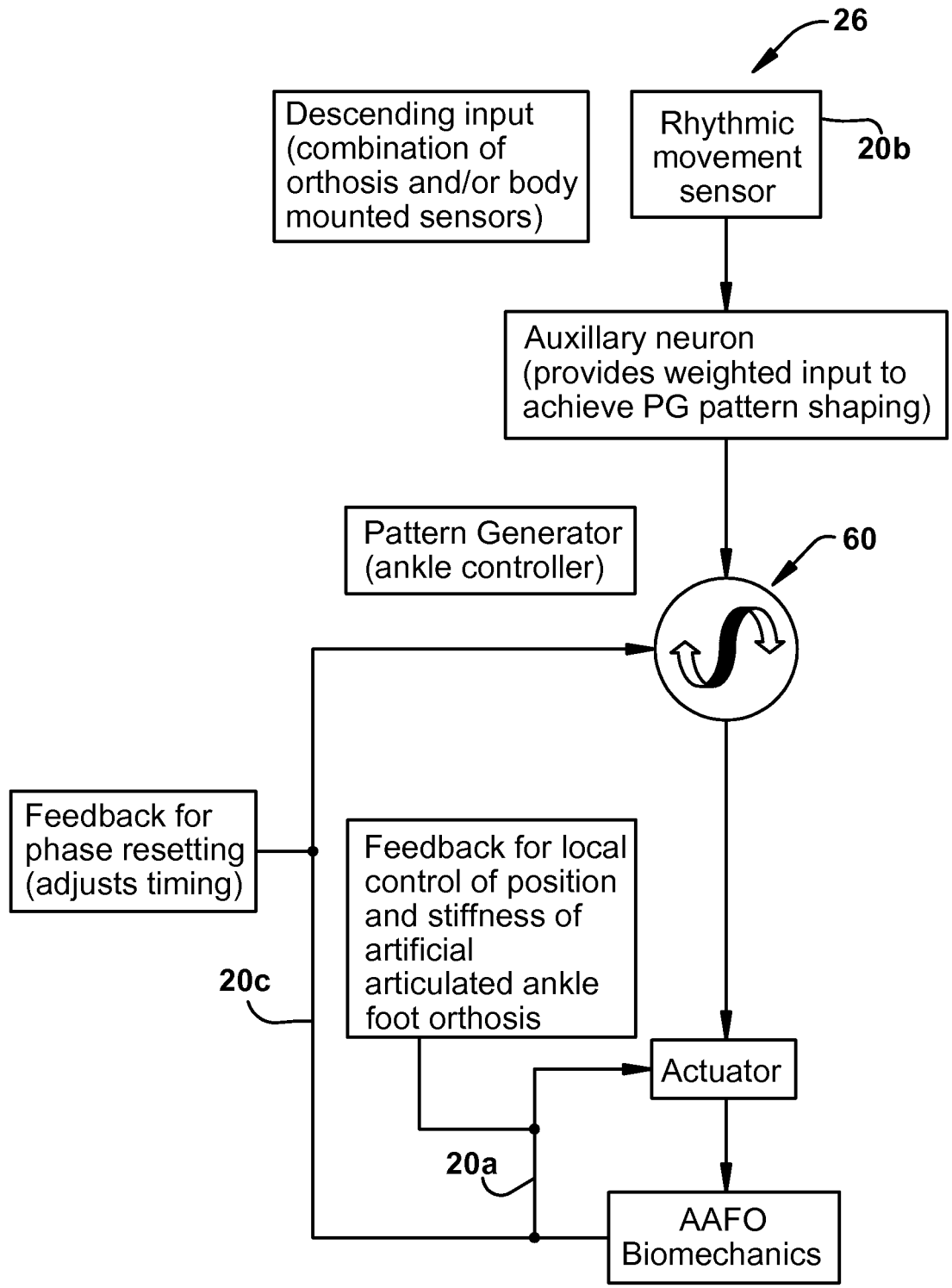
FIGS. 20 and 21 are flow charts schematically representing the sensor inputs and pattern generator used in the neuromorphic controlled powered orthotic device of the present application.
Figure 21:
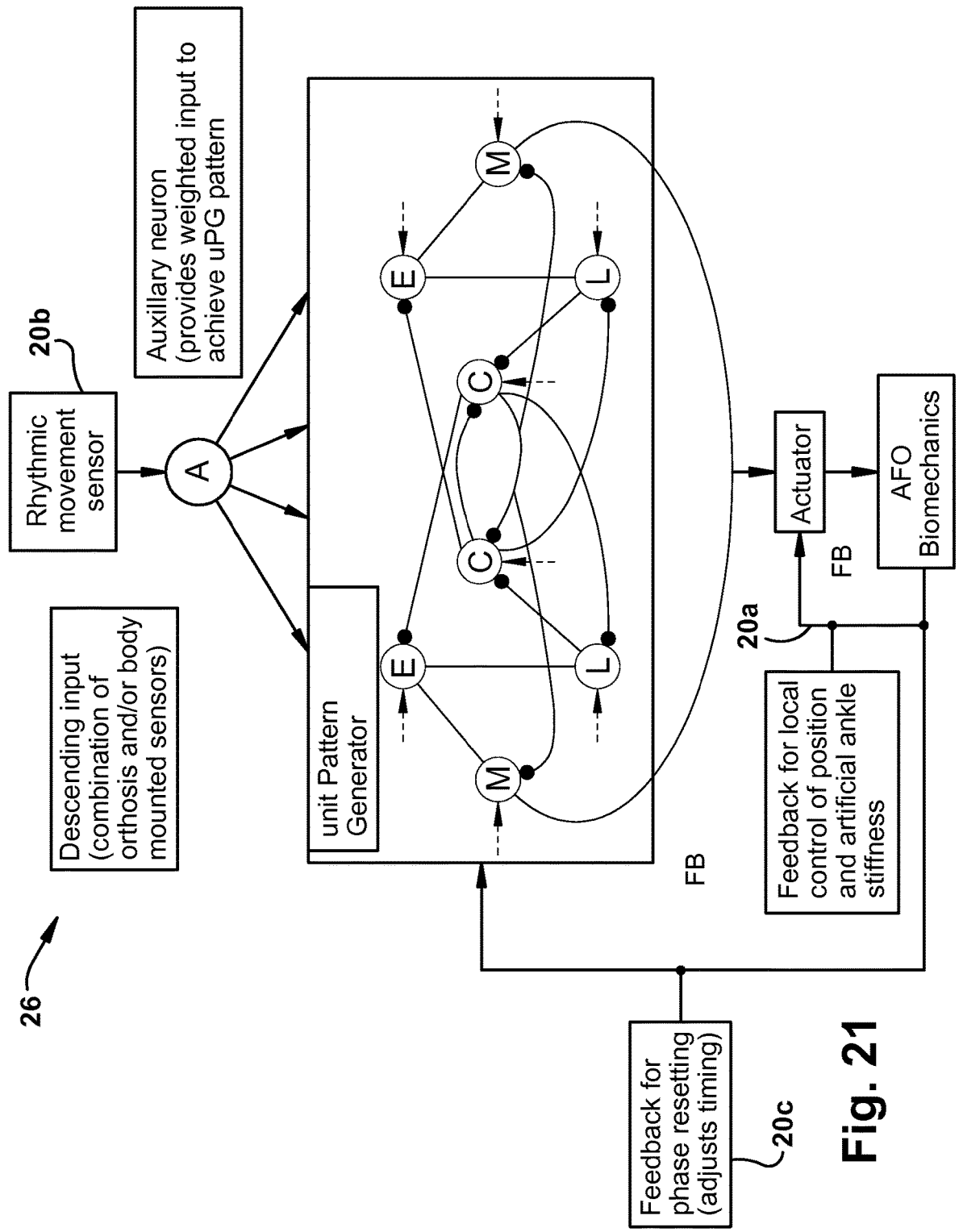

The NOCS 10 system controller 24 includes an electronic pattern generating circuit 26 which was developed based on the simplified connectivity pattern of neurons forming a neural network within the spinal cord of a primitive vertebrate, specifically a lamprey eel, to produce a rhythmic pattern for signaling the actuator 22 to move the AAFO 18, and associated electronic circuitry to receive inputs from sensors, provide 24 V DC to 5 V DC voltage converter from the power source and to provide impedance matching between the controller 24 and the actuator motor controller 47. The neural network design within the electronic pattern generating circuit, together with the other discrete electronic components are provided as the NOCS system controller, which are enabled in a portable unit capable of being worn by a user S are as shown in FIG. 3, and hereafter referred to as a pattern generator PG. This controller 24 and the power supply 32 fit within a belt pouch or back pack C, as shown schematically in FIG. 3. The basic connectivity pattern employed by the pattern generator is shown in FIGS. 20-21.

The neural network structure of the PG is based upon a 9-neuron network mimicking the simplified connectivity pattern of spinal cord neurons in primitive vertebrates to produce rhythmic movement output. The 4 types of neurons on each side of the body, or 8 in total, are the excitatory E, lateral L, crossed C and motor M. An auxiliary neuron A is also used. An auxiliary neuron (A) was added to the PG circuit to provide input to the constituent neurons for entrainment of the PG output to an external signal. The external signal will be a voltage proportional to one of the continuous gait measure signals. The A neuron modifies this voltage to a current to be injected into one of the other eight neurons. The number of neurons used to form a network, besides the A neuron, can be modified to fewer neurons, or a single neuron on each side, or the 8-neuron network may be replaced by a single neuron. Thus, the network oscillator 60, shown schematically in FIG. 20, may consist of two or more neurons. The neurons may or may not be arranged in a symmetric pattern. A non-symmetric pattern would mimic networks found in invertebrates. A single neuron that is capable of producing rhythmic output could replace the network of 8 or fewer neurons. In the latter case the mathematical model used for defining the neuron itself must include pacemaker currents, not shown.

Each neuron provides a periodic output signal that can be utilized to provide the periodic drive signal to the actuator motor controller 47. All neurons of the PG 26 are driven by a constant tonic input and one or more neurons of the PG are driven by a phasic input, obtained from signal data capturing from the sensors 20 during walking movement. The dynamic activity of each neuron is described by the following differential equations.

In the preferred embodiment, each neuron is described by the following differential equation example:

$$C_M^i \frac{dv_i}{dt} = G_R^i(V_R^i - v_i) + G_T^i(V_T^i - v_i) + \sum_j G_{ji} h(v_j)(V_{syn}^j - v_i) + G_{ext}^i(V_{ext}^i - v_i) + Ipm + Iext$$

where $v_i$ is the membrane voltage of neuron i,
$C_M^i$ is its membrane capacitance,
$G_R^i$ is the maximum conductance across the membrane for passive currents flowing at rest,
and $V_R^i$ is the resting potential for neuron i,
$G_T^i$ is the maximum conductance for tonic synaptic input into the neuron i and $V_T^i$ is the reversal potential for the tonic current input,
$G_{ji}$ is the maximal synaptic conductance for phasic synaptic input from neuron j to neuron i, and $V_{syn}^i$ is the synaptic reversal potential for the synaptic current from neuron j to i,
$G_{ext}^i$ is the maximal synaptic conductance for external input, and
$V_{ext}$ is the reversal potential for the conductance on the external input. This external input is the output of one or more sensors.

Ipm are other pacemaker currents that allow a single neuron to produce cyclic voltage output and may or may not be used.

Iext are injected currents in proportion to the sensor outputs.

Each neuron's output represents the firing frequency and is assumed to be related to its membrane voltage by a nonlinear function given by a seventh order polynomial h(v) with a strict threshold and saturation.

$$\begin{aligned} h(v) &= -20v^7 + 70v^6 - 84v^5 + 35v^4 \text{ for } 0 \le v \le 1 \\ &= 0 \quad \text{for } v \le 0 \\ &= 1 \quad \text{for } v \ge 1 \end{aligned}$$

With these membrane properties and the interconnections shown in FIGS. 20-21, under appropriate constant tonic drive the preferred embodiment of the PG of the present application generates:
 a left-right alternating oscillatory rhythm;
 stable oscillations over a range of frequencies spanning normal human walking, or approximately 0.1 Hz to 3 Hz; and
 has a capacitive membrane with transmembrane conductances that provide pathways for passive leakage current, tonic drive current, synaptic current from other PG neurons and external current from sensor 20a, 20b, 20c derived signals.

The output voltages of the PG are scaled to lie between 0 and 5 volts. The cyclic output from the PG 26 provides feedforward or open loop input to the motor controller 47 of the actuator 22 connected to the AAFO 18. Descending voluntary control of the user S, which is determined based upon rhythmic lower limb L movement detected by sensors 20, such as the sensor on the injured limb or the in-body or on-body sensors on the injured or uninjured (opposite) limb, provides an input signal to the PG to initiate or terminate the rhythmic control of the AAFO 18 using the motor controller 47 of the actuator 22, thereby capturing the user's intent to move. Such analog cycle-to-cycle control or entrainment of the PG rhythm through an electronic auxiliary neuronal circuit is used to match AAFO 18 motion or rhythm to a self-selected walking speed.

Sensors 20b on the AAFO 18 or user S, or an encoder within the motor controller 47 driving the actuator, provide a feedback signal FB to the motor controller 47 of the actuator 22 to provide closed loop control of the false-foot 16 position and stiffness, in combination with the feedforward drive signal from the PG.

Sensors 20b on AAFO provide feedback FB to the PG for phase dependent resetting, or adjustment of the cycle period, which is dependent on the phase of the cyclic movement or of the cyclic output of the PG, in response to external disturbance. During such phase dependent resetting, the actuator 20 causes the AAFO 18 to plantar-flex and/or dorsi-flex.

It should be understood that the PG 26 and auxiliary or 'A' neuron in FIG. 21 can be implemented in either software or in hardware embodiments. Software implementation can be supported in computer which can be worn in backpack to provide tethered control of AAFO. However, to make use of a more portable or tetherless NOCS shown in FIG. 3, a hardware embodiment of the present application is necessary.

In either embodiment, the PG 26 can work as an autonomous oscillator, meaning that it does not need periodic drive signal input from the sensors 20a, 20b, 20c, to enable oscillation. The PG oscillations can be suppressed if there is a constant external signal input to the PG. Additionally, the NOCS speed of operation can be entrained to an external signal input from the sensors 20 to the PG. The PG responds to external changes in speed within a cycle of perturbation. Additionally, no programming if-then rules are used to adjust the PG signal output. The PG could also be programmed to respond to simultaneous inputs from more than one entrainment and/or perturbation signal, and thus can be entrained and respond to brief perturbations at the same time. If more than one PG is used, and were provided in appropriate phase relationship, a knee and ankle prosthesis could both be controlled at the same time.

Alternatively, in other embodiments it may be desired to use the PG to drive other cyclic processes, which maybe physiological or not, and which are not locomotor related. Still other examples of locomotor related applications, involve use of the PG to control an articulated actuated ankle foot orthosis, where the powered articulated false-foot 16 connects to an ankle and acts as a robotic assist device for therapy of the injured ankle The PG could be used without any input from the user S in a passive mode of exercise or could be entrained by signals from on-body sensors or in-body sensors, such as neural cuff, as the person is walking, to entrain the PG to provide active control of the articulated actuated ankle-foot orthosis.

The PG is simulated for oscillation, and has the ability to be entrained at a variety of frequencies that would be within the range of human walking speed. Current in proportion to the amplitude of a simulated phasic input was provided and the PG oscillation frequency monitored. Under default conditions, the PG oscillates at a pre-entrainment default frequency ($f_{pre}$) of 0.75 Hz. Once entrainment begins, the PG circuit quickly assumes the frequency ($f_{post}$) of the current input. The PG circuit can thus be entrained to a 1:1 ratio ($f_{post}/f_{pre}$).

Figure 22:
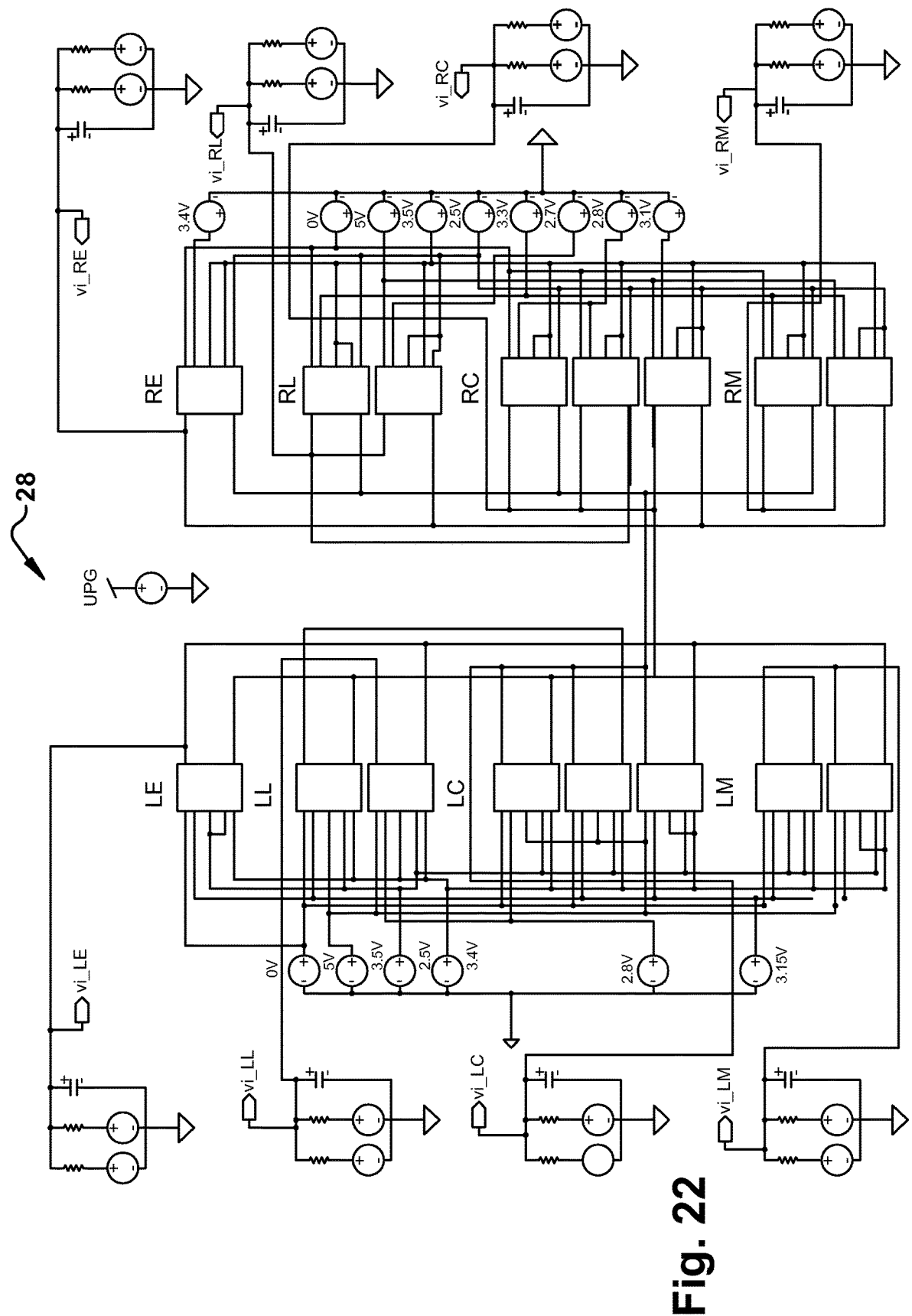
FIG. 22 is a schematic representation of the electronic circuit of the pattern generator used in the neuromorphic controlled powered orthotic device of the present application.
Figure 23:
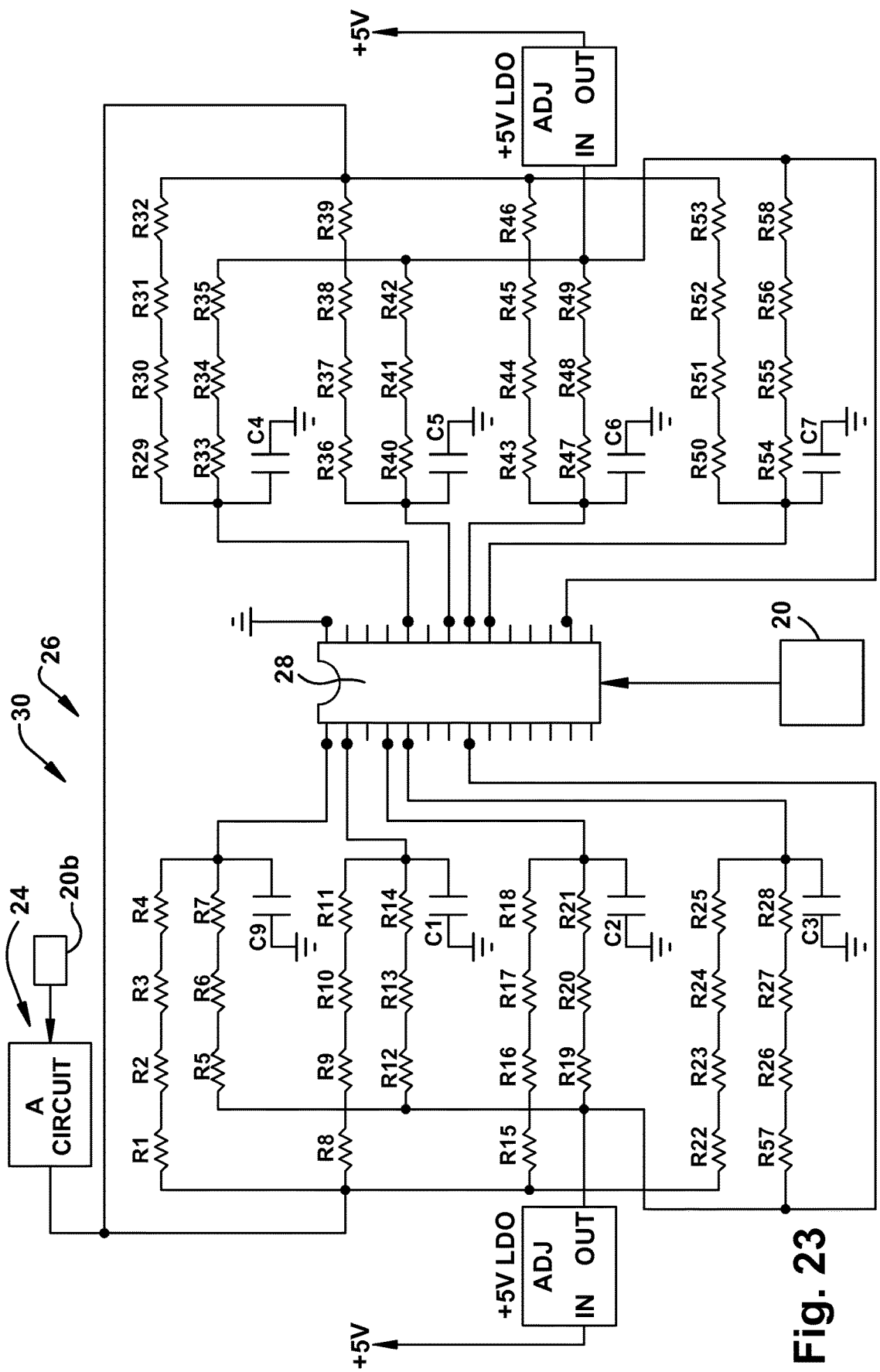
FIG. 23 is a schematic representation of the electronic circuitry within the system controller of the neuromorphic controlled powered orthotic device of the present application.

FIGS. 22 and 23 show schematic components of a preferred circuit with the synaptic interconnects between the 8 neurons in the PG implemented using a 28 pin, analog VLSI chip 28 and discrete components and other circuitry provided on a circuit board 30 made from components as described and shown. The frequency of oscillations of all the neurons of PG circuit is ideally 0.75 Hz, but within a range of approximately 0.1-4 Hz. The analog VLSI chip 28 is manufactured using an AMI 0.5 μm complementary metal-oxide-semiconductor process of the type processed by MOSIS, but could be implemented in other analog VLSI technology processes ranging from 0.13 to 1.5 μm or in nanometer technology processes such as 90 nm. The supply voltage can range up to 5 volts depending on the process used. The sub-circuits of the system include differential circuits, p-MOS, n-MOS, current mirrors and wide range amplifiers. The PG circuit uses 467 transistors and the VLSI circuit layout size is just 6.071 sq millimeters.

Noise is important in all analog circuits because it limits dynamic range. Some common techniques were included in the PG design to reduce noise, such as multi-gate finger layout, inter-digitization, substrate plugging and a common-centroid layout.

The PG 26 design operates using a voltage of approximately 5V, but which can range from about 1.2V to 5V, and is capable of battery operation. The design operating temperature range is approximately −55 deg C. to +125 deg C. The chip 28 is packaged using commercially available techniques but preferably uses a ceramic DIP package that when plugged into a DIP socket, can be replaced, stored, or transferred from one board to another. The current chip utilizes ceramic DIP packaging.

Figure 24A:
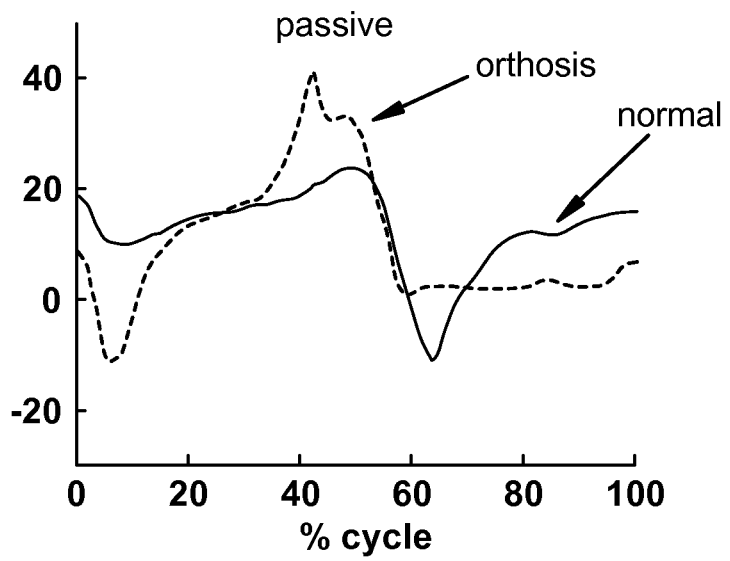
FIG. 24a is a graphical representation of the sensed movement during walking of a normal limb and a limb with a non-operable/passive NOCS.
Figure 24B:
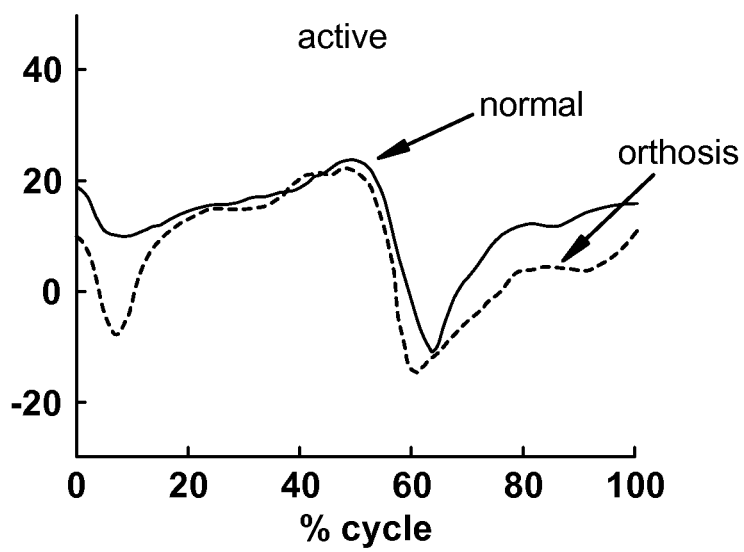
FIG. 24b is a graphical representation of the sensed movement during walking of a normal limb and a limb with an operable/active NOCS.

To ensure the capture of signals regarding intent to move and environmental conditions, trials were conducted during which the user S walked over a foot high obstacle with the limb with the active NOCS. The user S did not stumble and the false-foot 16 remained in position during the step over the obstacle. When a subject walked with a passive/off orthosis there was left-right asymmetry in gait kinematics as shown in the left graph of FIG. 42*a*. With an active/on NOCS this asymmetry is improved and the pattern moves towards a normal pattern, as shown in the right graph of FIG. 24*b*.

Figure 25A:
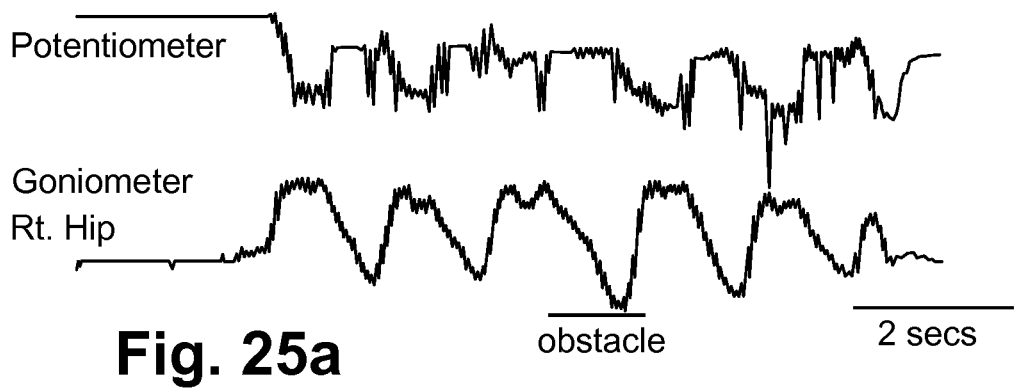
FIGS. 25a and 25b are graphical representations of the sensed movement during walking using the NOCS.
Figure 25B:
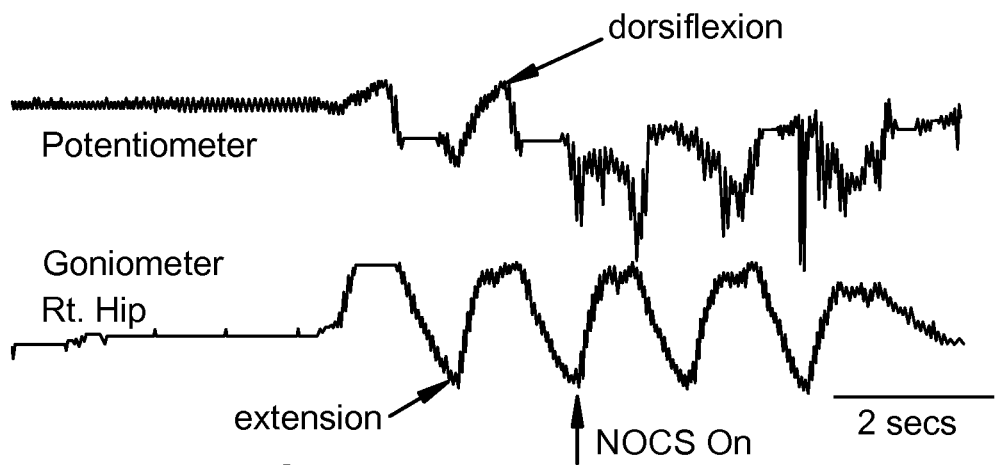

As shown in FIGS. 25*a*, 25*b*, the NOCS allows cycle-to-cycle adjustment of gait without conscious effort by the user. FIG. 25*b* shows transition from passive to active control while the subject was walking at a self-selected speed. In the passive/off mode the potentiometer recording shows the excessive dorsi-flexion before push-off which is converted to the appropriate plantar-flexion by the active/on NOCS. The controller responds immediately with appropriate adjustment of the step cycle.

Figure 26:
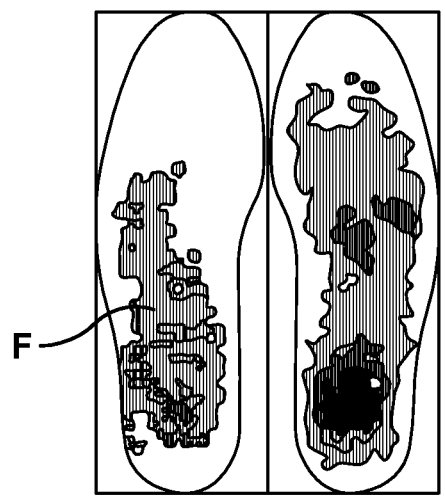
FIG. 26 is a graphical representation of the forces on the feet of a user during walking with the NOCS of the present application.

FIG. 26 shows the pressure distribution under the feet during walking with the active NOCS. The left foot F is immobilized using the NOCS while the right foot F is in direct contact with the walking surface. The pressure distribution indicates that the transmission of force from the false-foot 16 to the immobilized foot F is reduced under the heel and forces are not transmitted to the ball of the foot. In general, load bearing of the immobilized foot during the gait cycle is lower. Additionally, operation of the NOCS 10 may be further enhanced where an commercially available boot is also worn on the non-injured limb.

The foregoing descriptions of various aspects of the device of the present application have been presented for purposes of illustration and description. It is not intended to be exhaustive or to limit the invention to the precise form disclosed, and obviously, many modifications and variations are possible. Such modifications and variations that may be apparent to a person skilled in the art are intended to be included within the scope of the invention as defined by the accompanying claims.

We claim:

1. A system for generating a neuromorphic signal pattern for use as a control signal in a powered assistive false-foot configured to surround and support a foot within footwear of a lower limb for assisting a user wearing the powered assistive false-foot, comprising, a controller having an electronic pattern generating circuit with a biomimetic design that mimics the simplified connectivity of a 9-neuron network within the spinal cord of primitive vertebrates, wherein the electronic pattern generating circuit is made from analog integrated components and discrete electronic components and is configured to generate an autonomous signal for initiating movement of the powered assistive false-foot; and a surfaces sensor supported on the powered assistive false-foot for detecting changes in the powered assistive false-foot and a surfaces sensor supported on the user wearing the powered assistive false-foot, and the surfaces sensors are configured to provide the changes detected to the controller having the electronic pattern generating circuit with the biomimetic design which generates an autonomous signal for adjusting the signal pattern output of the system to match the sensed changes.

2. A powered device for assisting a user with walking, comprising:
- a controller for controlling movement of the powered device having an electronic circuit with a biomimetic design that mimics the connectivity of neurons within the spinal cord of primitive vertebrates, wherein the electronic circuit is an electronic pattern generating circuit is made from analog integrated components and discrete electronic components and is configured to generate an autonomous signal;
- an actuated articulated false-foot configured to connect to, surround, and support a foot within footwear of an injured lower limb within the articulated false-foot to form an actuated articulated false-foot prosthesis;
- a linear actuator supported between an upper attachment location, and a lower attachment location on the actuated articulated false-foot for driving the articulated false-foot prosthesis; and
- a sensor mounted on the articulated false-foot to sense movement of the articulating false-foot prosthesis.

3. The powered device for assisting a user with walking of claim 2, wherein the controller is configured to automatically start and stop movement of the actuated articulated false-foot prosthesis.

4. The powered device for assisting a user with walking of claim 2, wherein the controller is configured to automatically move the actuated articulated false-foot prosthesis at a user selected walking speed.

5. The powered device for assisting a user with walking of claim 2, wherein the controller is configured to automatically respond to external environmental input to adjust the movement pattern of the actuated articulated false-foot prosthesis.

6. The powered device for assisting a user with walking of claim 2, wherein the device is portable and is configured to be carried by the user.

7. A powered device for assisting a user with walking, comprising:
- a controller for controlling movement of the powered device, the controller having an electronic circuit with a biomimetic design that mimics the connectivity of neurons within the spinal cord of primitive vertebrates, wherein the electronic circuit is an electronic pattern generating circuit made from analog integrated components and discrete electronic components and is configured to generate an autonomous signal;
- an actuated articulated false-foot configured to connect to, surround and support a foot within footwear of an injured lower limb within the articulated false-foot to form an actuated articulated false-foot prosthesis;
- a linear actuator supported on the powered device for driving the articulated false-foot prosthesis; and
- a sensor mounted on the articulated false-foot and a surface sensor configured to be mounted on the user to sense movement changes, and the sensors configured to provide sensed movement changes detected to the controller for adjusting the signal pattern output of the controller to match the sensed movement changes.

* * * * *